United States Patent [19]

Martin et al.

[11] Patent Number: 4,887,721

[45] Date of Patent: Dec. 19, 1989

[54] LASER PARTICLE SORTER

[75] Inventors: John C. Martin; Tudor N. Buican, both of Los Alamos, N. Mex.

[73] Assignee: The United States of America as represented by the United States Department of Energy, Washington, D.C.

[21] Appl. No.: 126,156

[22] Filed: Nov. 30, 1987

[51] Int. Cl.⁴ .............................................. B07C 5/342
[52] U.S. Cl. .................................... 209/579; 209/3.1; 209/606; 356/72
[58] Field of Search ................. 209/3.1, 3.3, 579, 606; 356/39, 72, 73

[56] References Cited

U.S. PATENT DOCUMENTS 3,710,279  1/1973  Ashkin ................................ 331/94.5
3,808,550  4/1974  Ashkin ................................ 331/94.5

OTHER PUBLICATIONS

Tudor N. Buican et al., "Automated Single-Cell Manipulation and Sorting by Light Trapping," 26 Applied Optics, No. 24, 5311–5316 (15 Dec. 1987).
A. Ashkin et al., "Observation of Light Scattering from Nonspherical Particles Using Optical Levitation," 19 Applied Optics, No. 5, 660–668 (1 Mar. 1980).
A. Ashkin et al., "Optical Levitation by Radiation Pressure," 19 Applied Physics Lett., No. 8, 283–285 (15 Oct. 1971).
A. Askin et al., "Acceleration and Trapping of Particles by Radiation Pressure," Phys. Rev. Lett. 24, No. 4, pp. 156–159 (Jan. 26, 1970).
A. Askin, "Applications of Laser Radiation Pressure," Science 210, No. 4474, pp. 1081–1087 (Dec. 5, 1980).
A. Askin et al., "Optical Trapping and Manipulation of Viruses and Bacteria," Science 235, pp. 1517–1520 (Mar. 20, 1987).

Primary Examiner—Joseph J. Rolla
Assistant Examiner—Edward S. Ammeen
Attorney, Agent, or Firm—Ray G. Wilson; Paul D. Gaetjens; William R. Moser

[57] ABSTRACT

Method and apparatus for sorting particles, such as biological particles. A first laser defines an optical path having an intensity gradient which is effective to propel the particles along the path but which is sufficiently weak that the particles are not trapped in an axial direction. A probe laser beam interrogates the particles to identify predetermined phenotypical characteristics of the particles. A second laser beam intersects the driving first laser beam, wherein the second laser beam is activated by an output signal indicative of a predetermined characteristic. The second laser beam is switchable between a first intensity and a second intensity, where the first intensity is effective to displace selected particles from the driving laser beam and the second intensity is effective to propel selected particles along the deflection laser beam. The selected particles may then be propelled by the deflection beam to a location effective for further analysis.

12 Claims, 2 Drawing Sheets

LASER PARTICLE SORTER

This invention is the result of a contract with the Department of Energy (Contract No. W-7405-ENG-36).

BACKGROUND OF THE INVENTION

This invention relates to the manipulation of particles and, more particularly, to the use of lasers to manipulate and sort particles, such as biological cells.

The physical manipulation of single cells selected on the basis of their individual properties plays an important role in experimental cell biology and immunology, as well as in other areas of biomedical research. Two techniques, flow sorting and micromanipulation, have been used in a wide, albeit mutually exclusive, way for the purposes of cell separation or positioning. Flow sorting allows fast, automated, and essentially nonmechanical separation of cells with given optical and electrical phenotypes. However, both electrostatic and fluidic switching flow sorters divert a volume of fluid containing the cell of interest, rather than the cell itself, and thus, have limited positional accuracy. Micromanipulators can position selected cells with micron accuracy, but employ mechanical devices requiring relatively large open volumes for unhindered operation.

Light trapping has also been used to tray and manipulate viruses and bacteria. See, e.g., A. Ashkin. et al., "Optical Trapping and Manipulation of Viruses and Bacteria," Science 235, 1517-1520 (March 1987), hereinafter referred to as the "Ashkin reference," and incorporated herein by reference. Optical trapping is based on the transfer of momentum between microscopic particles and the photons they scatter. While the forces produced by this interaction are extremely small, so are the other forces, such as weight and viscous drag, which act on a microscopic particle suspended in a stationary or slowly moving fluid.

Under suitable conditions, the interaction between a collimated laser beam and a microscopic particle results in a radial force proportional to the gradient of beam intensity and in the direction of the intensity gradient, and in an axial force proportional to beam intensity and directed along the beam axis. The radial force can act as a restoring force that traps the microscopic particle on the beam axis. In a strongly focused laser beam, as taught by the Ashkin reference, the axial force may change sign at a point close to the beam waist, and a full three-dimensional trap results. Short focal length optics are provided and the trap is limited to a small volume close to the focus point. Thus, the particles are trapped about the focus and cannot move along the beam axis for transport.

The limitations in the prior art are addressed by the present invention and an improved laser system is provided for identifying and sorting biological particles.

Accordingly, it is an object of the present invention to accurately position biological particles without mechanical contact with the particles.

It is another object of the invention to optically identify and sort a stream of biological particles.

It is yet another object of the invention to sort biological particles with minimum effect on the particles.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF INVENTION

To achieve the foregoing and other objects, and in accordance with the purposes of the present invention, as embodied and broadly described herein, the apparatus of this invention may comprise an apparatus for sorting particles. A first optical means is provided for propelling the particles along a preselected path. A second optical means defines a deflection path which intersects the propulsion path at an angle and deflects selected particles to a location outside the propulsion path.

In another characterization of the present invention, a method is provided for sorting particles. Particles are radiatively propelled along a propulsion path, where particles are identified which have preselected phenotypical characteristics. The identified particles are then radiatively deflected along a path intersecting the propulsion path for elution and analysis.

In one other characterization of the present invention, a method is provided for optically transporting particles. A weakly focused laser beam defines a propulsion path having an axial beam intensity gradient effective for transporting the particles but ineffective for axially trapping particles.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

According to the present invention, laser beams and radiative pressure effects are used to perform cell sorting. Interactions between particles of various sizes and the photons in a collimated light beam lead to a transfer of momentum between photons and particles and thus to radiation forces. Experimental results, such as the Ashkin reference, have confirmed that light beams can easily be produced such that the radiation forces stably trap the particles.

As herein described, beam propulsion and guiding of particles can be used to (i) move individual particles through the measurement volume; and/or (ii) narrowly confine the particles along the beam axis while measurements are performed; and/or (iii) deflect and guide selected particles toward collection areas. In accordance with the present invention, it is found that particles can be propelled over useful distances using a weakly focused laser beam, i.e., a focus which provides an axial intensity gradient that is insufficient to trap particles adjacent the focal point.

In a composite arrangement for particle sorting, a driving beam formed by a collimated laser beam intersects a deflection beam similarly obtained from a laser beam. Particles are suspended in a fluid, trapped by the driving beam, and guided to the intersection with the deflection beam. If the relative intensities of the two beams are correctly chosen, then the particles are deflected and propelled in the direction of the deflection beam. If the deflection beam is not activated, the particles continue along the driving beam.

Figure 1:
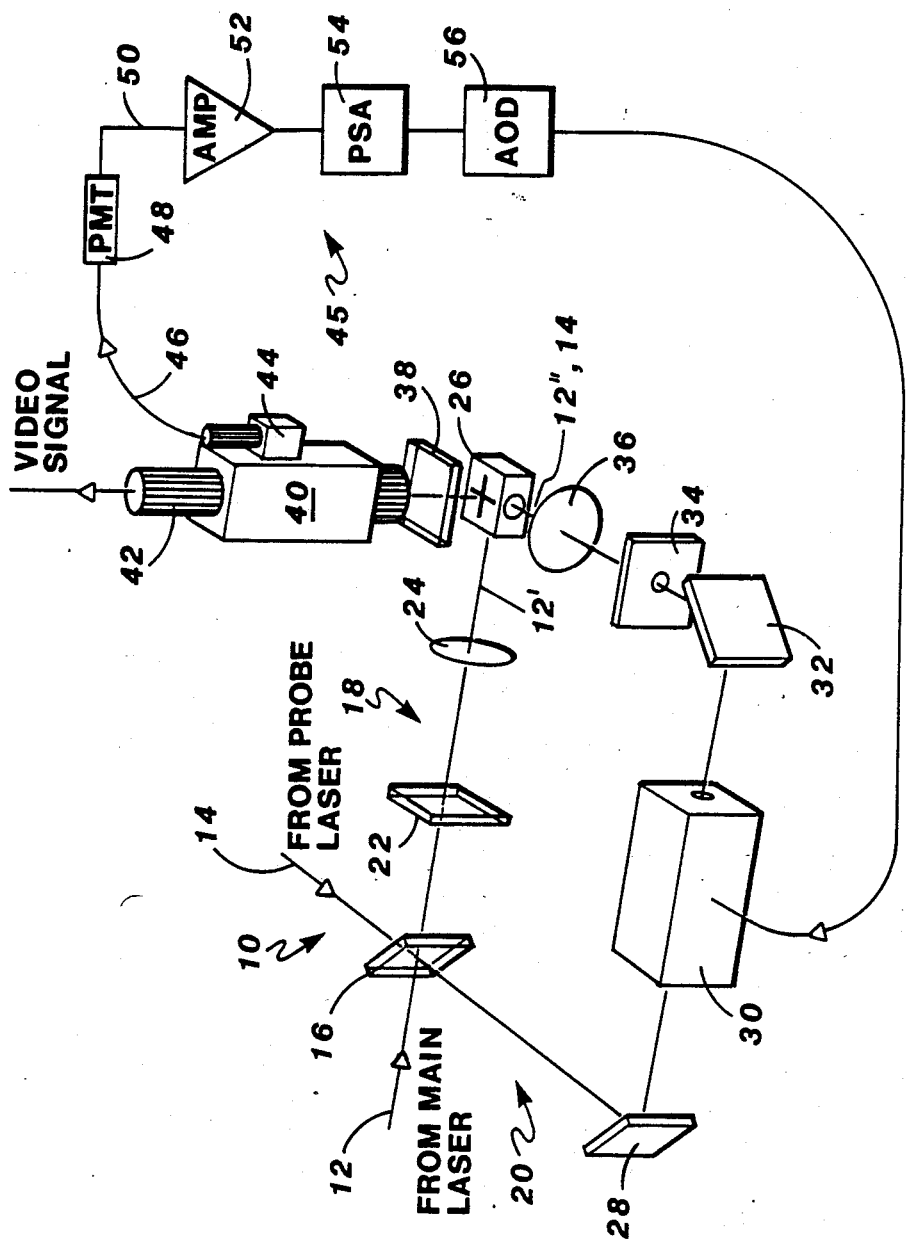
FIG. 1 is a pictorial illustration in block diagram form of one embodiment of a particle sorter according to the present invention.

FIG. 1 illustrates an implementation of a particle sorter 10 based on laser beam propulsion and deflection of individual particles. Particles are injected in manipulation chamber 26, where they are trapped and propelled by collimated propulsion beam 12'. One or several detector systems 45 measure parameters of interest (particle volume, light scattering intensity, fluorescence, etc.). The video signal output from camera 42 can also be used directly to analyze particle characteristics and behaviors.

The output of a detector 48 is processed by electronic circuitry, such as amplifier 52 and analyzer 54, and a sorting decision is taken on the basis of measured parameter values. In one embodiment, intensity modulator 30 is controlled by the system driver 56 and is used to switch the intensity of deflection beam 12''. Depending on the state of this beam, the particle is propelled into a collection region within manipulation chamber 26 to be removed for further analysis.

In a particular embodiment of the present invention, the propulsion and deflection beams 12', 12'' are derived by means of a beam splitter 16 from the same main laser 12, which may be an argon ion laser (Spectra-Physics, Mountain View, Calif.) operating at 488 nm. Deflection beam 12'' passes along beam path 20 and is aligned by mirror 28 for passage through acoustooptic modulator 30 (NRC, Fountain Valley, California), which splits beam 12'' into several diffracted beams that are directed toward aperture 34 by mirror 32. Aperture 34 allows only the zero order beam to reach manipulation chamber 26. A probe beam 14 is generated by a low power probe laser, which may be a HeNe laser at 633 nm, for use in particle identification. Probe beam 14 travels along beam path 20 and is blocked along propulsion beam path 18 by a short-pass filter 22, e.g., a 500 nm filter. planoconvex lenses 24, 36 (50 mm focal length) focus propulsion beam 12', deflection 12'' and probe 14 beams.

An observation device 40, which may be a stereo microscope (Model SZH, Olympus, Japan), is placed above manipulation chamber 26. Observation and measurement within chamber 26 may be through a video system 42. Long-pass filter 38, e.g., 515 nm, may be placed before microscope 40 to block the light scattered from the main beams 12', 12''. Detector 48 may be provided with observation device 40 for direct optical measurements of phenotypical events within chamber 26. Optical fiber 46 connects optical pickup 44 to photomultiplier tube 48 (EMI 9798QB) for optical measurements, e.g., measuring 90° light scatter. The output 50 of photomultiplier tube 48 is amplified 52 for analysis by a pulse shape analyzer 54.

Typical event parameters include pulse height, pulse width (interval between threshold crossing points), and number of threshold crossings. In one embodiment, the logical conditions for activating deflection beam 12'' are that (i) the pulse height be within a preset window; (ii) the pulse width be shorter than a preset value; and (iii) the number of threshold crossings in the positive direction within a preset interval be less than two. These conditions ensure that a decision to deflect is not made when two or more particles are present in the measurement region. The logic output of analyzer 54 controls acoustooptic modulator driver 56 and the intensity of deflection beam 12'' through acoustooptic modulator 30.

Figure 2:
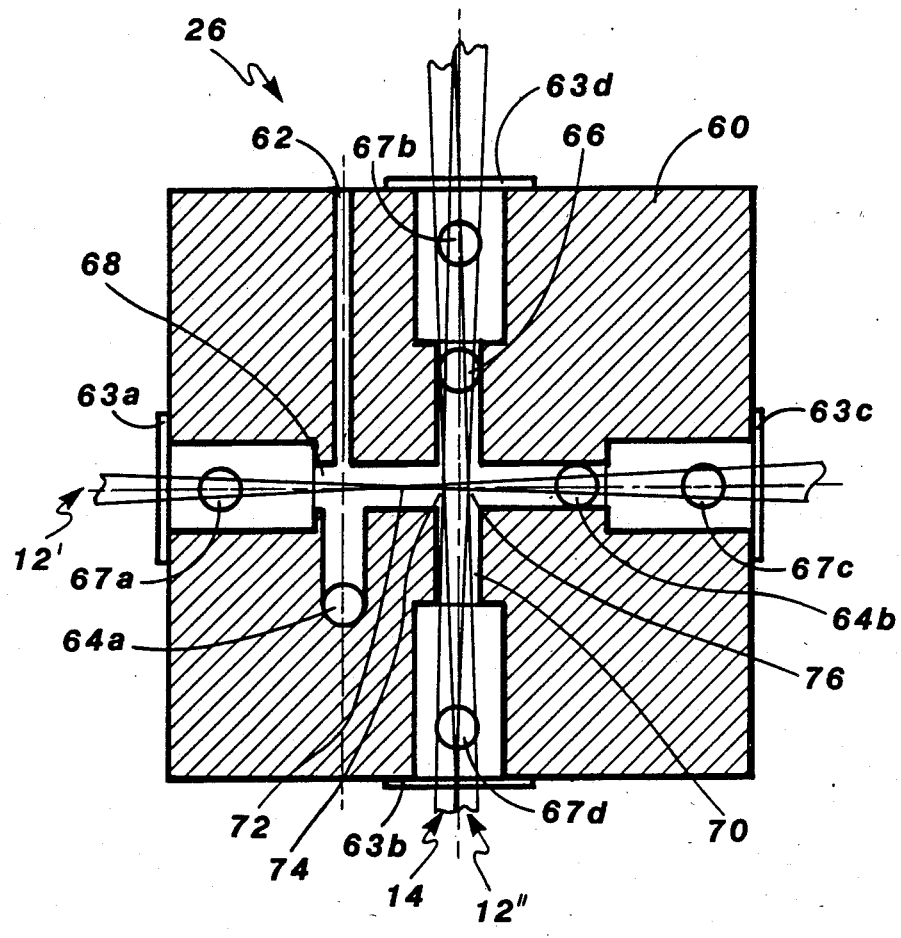
FIG. 2 is a cross-sectional view of a manipulation chamber for particle identification and sorting.

Referring now to FIG. 2, there is shown in cross section one embodiment of manipulation chamber 26, where cell analysis and manipulation take place. Chamber body 60 may be constructed out of brass and defines propulsion channel 68 and deflection channel 70, which are narrow channels (1 mm wide and 3.5 mm deep) machined into the upper surface of the chamber. A thin, flat glass window (not shown) covers chamber 26 and allows observation and optical measurements to be performed. Additional windows 63a, 63b, 63c, 63d on the four sides of chamber 26 are provided for propulsion beam 12' and deflection beam 12'', as well as for additional probe beams 14. Small diameter stainless steel tubing (not shown) is attached to sample inlet port 62 and to outlet ports 64a, 64b, deflection outlet port 66, and rinse ports 67a, 67b, 67c, 67d.

A particle suspension of suitable concentration is injected 62 at low speed into propulsion channel 68, along propulsion beam 12'. The particles are trapped by beam 12' and travel along the beam axis. The injection region is followed by a measurement region, where the probe beam 14 intersects the propulsion beam 12'. In one embodiment, the intensity of light scattered by the cells is measured in a direction perpendicular to that of probe beam 14. Following the measurement region, propulsion beam 12' intersects deflection beam 12''. The intensity of deflection beam 12'' can be switched between two levels, which are on either side of the threshold value for deflection determined by the geometry of the beams. The lower intensity level is still high enough for the deflection beam to propel and guide the deflected particles toward elution port 66. A second port 64b also allows the undeflected particles to be eluted.

Propulsion beam 12' and deflection beam 12'' are both weakly focused beams that radially trap particles within the beam, but that propel particles along the beam axis without axial trapping. In one embodiment, the beam waist diameters 72, 76 of the propulsion and deflection beams 12', 12'', respectively, are each 26 $\mu$m. The corresponding confocal parameter in water is 2.8 mm, which is comparable with the distance between sample injection port 62 and deflection beam 12''. Waist 72 of propulsion beam 12' lies between sample injection port 62 and probe beam 14, while waist 76 of deflection beam 12'' lies at the intersection of propulsion beam 12' and deflection beam 12''. This geometry, together with the choice of focal length for the focusing lenses, ensures that the injected particles reach the probe 14 and deflection 12'' beams in a relatively short time (5–10 s typically), and that the extraction of the particles by deflection beam 12'' can be reliably performed. The probe 14 and deflection 12'' beams intersect propulsion beam 12' at points defined by waists 74 and 76, respectively, approximately 100 $\mu$m apart.

An optical manipulator according to the present invention was tested with two types of particles: fluorescent polystyrene microspheres, and fluorescein isothiocyanate (FITC) stained Chinese Hamster ovary (CHO) cells. The polystyrene microspheres were surface-stained with FITC and had a diameter of 7.5 $\mu$m (Flow Cytometry Standards, Research Triangle Park, North Carolina). The CHO cells were collected while growing exponentially, and were fixed in ethanol and subsequently stained with 10 ng/ml FITC according to the procedure described by Crissman et al., "Rapid, One Step Staining Procedures for Analysis of Cellular DNA and Protein by Single and Dual Laser Flow Cytometry," Cytometry 3, 84–90 (1982).

Both polystyrene microspheres and CHO cells were consistently transported by the propulsion and deflection beams 12', 12" over distances of over 6 mm (the maximum length of the channel segments 68 and 70 opening to the surface of the chamber), at peak velocities of $6 \times 10^2$ and $5 \times 10^2$ μm/s, respectively. When the pulse shape analyzer 54 was activated, the device consistently deflected single particles (microspheres and CHO cells) for which the 90° light scattering pulse amplitude fell within the discriminator window.

An unexpected result was observed when trapping biological particles, e.g., live lymphocytes and fixed CHO cells. When several polystyrene microspheres were present in propulsion beam 12', the rearward particles would catch up with the forward particles and form aggregates. This may be explained by the fact that the rearward particles scatter a significant fraction of the beam away from the forward direction, and with a resultant decrease in the propulsion force and velocity of the forward particles. For the biological particles, however, the separation quickly decreases to a minimum value in the 50–150 μm range, which is thereafter maintained and the cells move with equal velocities.

On one occasion, three CHO cells aligned themselves in propulsion beam 12' and traveled over a distance of at least 6 mm while maintaining their separation. In this case, the distance between the upstream cell and the one in the middle was greater than that between the middle and downstream cells.

The stable lymphocyte and CHO cell configurations are essentially one-dimensional and the separation between adjacent particles is much larger than the particle diameter. The formation of a stable array with these properties may be due to the fact that the relative refractive indices of the cells in aqueous (phosphate buffered saline) suspension, typically 1.02–1.05, are considerably lower than those of polystyrene particles in water (1.20) or of liquid and solid particles in air.

In a geometric optics approximation, which should apply reasonably well to particles with diameters of the order of 10 μm, these cells behave like thick lenses which, because of their small relative refractive indices, have focal lengths considerably larger than the cell diameter. As a consequence, the propulsion beam is focused by cells at a distance several times the cell diameter (on the order of 10 μm for a CHO cell). Thus, the force exerted on a downstream particle may equal that exerted by the unperturbed beam, even when the separation between particles is of the order of 100 μm. According to the same approximation, a polystyrene microsphere will focus the beam at a point very close to its surface. Consequently, the separation between two such microspheres may have to be of the order of their diameters for a significant repulsive force to develop.

The optical manipulator herein described performs operations which are relevant to experimental cell biology. In particular, laser beams of fixed orientation were used to select cells with certain optical properties and to transport the selected cells over centimeter distances. It will be appreciated, however, that particle transport and selection according to the present invention are not limited to single, fixed laser beams. Multiple probe beams 14 may be provided to identify unique phenotypical characteristics in a mixed particle sample stream. Multiple deflection beams 12" may also be provided for deflecting particles at selected intervals along propulsion beam 12'. Deflection beam 12" may not be fixed relative to propulsion beam 12', but may intersect propulsion beam 12' at a variable angle for deflection as a function or particle properties identified by probe beam 14. Thus, very flexible experimental devices may be provided.

The observations published in the Ashkin reference, as well as the results herein, indicate that exposure of live cells to the light intensity level required for trapping does not result in visible cell damage. The above results were obtained with laser beam power levels of about 300 mW. While the beam power levels herein are about 60 times higher than those of the Ashkin reference for trapping motile bacteria, the beam waist diameters in the two systems are very different. The maximum power density in the propulsion beam according to the present invention is, thus, lower by an order of magnitude than the maximum power density in the trapping beam described by the Ashkin reference.

Only one optical measurement is herein described for use in automatic manipulation. However, it will be appreciated that many light scattering and fluorescence parameters, as well as nonoptical parameters, could be measured simultaneously and/or sequentially, and, because of the large amount of time available for these measurements, very good signal-to-noise ratios could be obtained. Moreover, such optical measurements need not be restricted to one small region inside the device. Indeed, compact charge-coupled (CCD) imaging devices could be used to measure simultaneously the position, optical properties, and even morphological features of several cells. Thus, a computer could track the positions and properties of a large number of cells, and thus ensure not only a large cell throughput, but also a very high level of confidence in the identity of the processed cells. This would be particularly important when identifying, sorting, and further manipulating rare cells and other biological particles.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for sorting selected particles from a variety of particles in a flow stream, comprising:

first optical means defining a first laser beam waist diameter effective for propelling said variety of particles along a preselected propulsion path;

second optical means defining a second laser beam waist diameter intersecting said propulsion path along a deflection path at an angle with said propulsion path and having an intensity effective for deflecting said selected particles to a location outside said propulsion path;

probe means for identifying a selected characteristic in said variety of particles; and modulation means responsive to said probe means for selectively activating said second optical means for deflecting particles with said identified characteristic.

2. Apparatus according to claim 1, wherein said probe means includes a laser beam intersecting said propulsion path at a location prior to said deflection path.

3. Apparatus according to claim 1, wherein said first and second beam waist diameters are each greater than the diameter of said particles in said flow stream.

4. Apparatus according to claim 1, wherein said modulation means includes means for switching said second optical means between a first intensity effective for displacing said particles from said propulsion path and a second intensity effective to propel said particles along said deflection path and ineffective to displace said particles from said propulsion path.

5. Apparatus according to claim 4, wherein said probe means includes a laser beam intersecting said propulsion path at a location prior to said deflection path.

6. Apparatus according to claim 4, wherein said first and second beam waist diameters are each greater than the diameter of said particles in said flow stream.

7. A method for sorting selected particles from a variety of particles in a flow stream, comprising the steps of:
  radiatively propelling said variety of particles along a propulsion path;
  irradiating said particles with a probe laser beam to derive an output signal functionally related to a preselected characteristic in ones of said variety of particles; and
  radiatively deflecting said particles with said preselected characteristic along a deflection path intersecting said propulsion path.

8. A method according to claim 7, further including the step of modulating a deflection laser beam with said output signal to effect said radiative deflection of said identified particles.

9. A method according to claim 8, wherein said step of modulating said laser beam includes the step of switching said deflection laser between a first intensity effective to deflect said identified particles along said deflection path and a second intensity effective to propel said deflected identified particles along said deflection path and ineffective to displace other ones of said particles from said propulsion path.

10. A method according to claim 7, wherein said step of radiatively propelling said particles includes the step of forming a laser beam having a waist diameter defining axial intensity gradients effective for transporting said particles, but ineffective for trapping said particles.

11. A method according to claim 8, wherein said step of radiatively propelling said particles includes the step of forming a laser beam having a waist diameter defining axial intensity gradients effective for transporting said particles, but ineffective for trapping said particles.

12. A method according to claim 9, wherein said step of radiatively propelling said particles includes the step of forming a laser beam having a waist diameter defining axial intensity gradients effective for transporting said particles, but ineffective for trapping said particles.

* * * * *